United States Patent [19]
Beattie et al.

[11] 4,296,111
[45] Oct. 20, 1981

[54] 7-SUBSTITUTED METHYL CEPHALOSPORINS DERIVATIVES AND ANALOGUES THEREOF

[75] Inventors: Thomas R. Beattie; Burton G. Christensen, both of Scotch Plains; Frank P. Dininno, Old Bridge, all of N.J.

[73] Assignee: Merck & Co. Inc., Rahway, N.J.

[21] Appl. No.: 48,551

[22] Filed: Jun. 14, 1979

Related U.S. Application Data

[63] Continuation-in-part of Ser. No. 815,475, Jul. 14, 1977, abandoned, which is a continuation of Ser. No. 634,082, Nov. 21, 1975, abandoned.

[51] Int. Cl.³ ............................................ C07D 501/00
[52] U.S. Cl. ...................................... 424/246; 544/16; 544/21; 544/24; 544/22
[58] Field of Search ........................ 544/21, 22, 24, 16, 544/27; 424/246

[56] References Cited

U.S. PATENT DOCUMENTS 4,123,539 10/1978 Dininno ............................... 424/270
4,150,156  4/1979 Beattie ................................... 544/21

Primary Examiner—Nicholas S. Rizzo
Attorney, Agent, or Firm—Frank M. Mahon; Hesna J. Pfeiffer

[57] ABSTRACT

Disclosed are antibiotic 7-(substituted methyl) cephalosporins, derivatives and nuclear analogues thereof; wherein the methyl substituent is, inter alia, hydroxyl, ketonic oxygen, imino nitrogen, amino or thio. Also disclosed are processes for the preparation of such compounds and their pharmaceutically acceptable salt, ester and amide derivatives; pharmaceutical compositions comprising such compounds; and methods of treatment comprising administering such compounds and compositions when an antibiotic effect is indicated.

3 Claims, No Drawings

7-SUBSTITUTED METHYL CEPHALOSPORINS DERIVATIVES AND ANALOGUES THEREOF

This is a continuation-in-part of application Ser. No. 815,475 filed July 14, 1977, now abandoned, which is a continuation of application Ser. No. 634,082, filed Nov. 21, 1975, now abandoned.

BACKGROUND OF THE INVENTION

This invention relates to a new class of antibiotics which may be generically represented by the following structural formula (I):

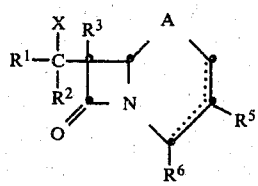

wherein the dotted line indicates provision for both $\Delta^2$ and $\Delta^3$ embodiments; A is S, O, $CH_2$, SO, or $NR^7$ ($R^7$ is selected from the group consisting of hydrogen, alkyl, formyl, acyl, thioacyl, alkylsulfonyl, and arylsulfonyl); X is OH, =O, SH, =NH, $NH_2$, $NHR^7$; $R^1$ and $R^2$ are independently selected from the group consisting of hydrogen; substituted and unsubstituted: alkyl, aryl, aralkyl, heteroaryl and heteroaralkyl (mono- and bicyclic) wherein the heterocyclic moiety comprises 4–10 ring atoms and the hetero atom (for atoms) is O, N or S; wherein the ring or chain substituent is selected from amino, carboxy, hydroxy, alkoxy, carbalkoxy, lower alkyl, heteroaryl, and substituted amino such as mono- and dialkylamino, and acylamino, and perhaloalkyl; examples of such substituents, $R^1$ and $R^2$ are: methyl, trifluoromethyl, phenyl, substituted phenyl, benzyl and the like. $R^3$ is selected from the group consisting of hydrogen, alkoxy, halogen, such as fluoro and bromo, and alkylthio; $R^6$ is selected from the group consisting of $PO(OH)_2$, $SO_2(OH)$, $SO_2NH_2$ and derivatives thereof [see co-pending commonly assigned U.S. Patent Application Ser. No. 410,831 filed Nov. 8, 1973, now U.S. Pat. No. 4,032,521, incorporated herein by reference for definition of $R^6$], and $COXR^8$ wherein X is oxygen or sulphur and $R^8$ is conventionally known in the cephalosporin and cephalosporin-like art and is, inter alia, representatively selected from the group consisting of hydrogen, trialkylsilyl, and the pharmaceutically acceptable salt, ester and amide moieties known in the art such as sodium, potassium, pivaloyloxymethyl, and the like; $R^5$ is hydrogen, chloro, alkoxy, formyl or $CH_2Y$, wherein Y is hydrogen, hydroxy, halo, mercapto, acyloxy, acylthio, substituted hydroxy, substituted mercapto, a quaternary ammonium group, azido, amino or a N-substituted amino group.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms—they are generally not effective against a broad range of pathogens.

Unexpectedly, it has been found that the compounds of the present invention are broad spectrum antibiotics, which are useful in animal and human therapy and in inanimate systems. It will be recognized from the above generic representation (I) that the principal novel feature of the compounds of the present invention is the 7-substituted methyl substituent, which position heretofore in the cephalosporin art has always been amino or substituted amino for compounds of high activity. It will also be noted, except where expressly stated, that the balance of the cephalosporin or cephalosporin-like structure (I) is well-known in the relevant art.

Thus, it is an object of the present invention to provide a novel class of antibiotics which inclues, inter alia, species having the basic nuclear structure of the cephalosporins but which are characterized by having a substituted methyl substituent at the 7-position of the β-lactam ring. These antibiotics are active against a broad range of pathogens which representatively include both gram positive bacteria such as Staphylococcus aureus and Streptococcus pyrogenes and gram negative bacteria such as E. coli and Klebsiella pneumoniae. Further objects of this invention are to provide chemical processes for the preparation of such antibiotics; pharmaceutical compositions comprising such antibiotics; and to provide methods of treatment comprising administering such antibiotics and composition when an antibiotic effect is indicated.

DETAILED DESCRIPTION OF THE INVENTION

The following co-pending commonly assigned U.S. Patent Application is incorporated herein by reference for the subject matter which it discloses as it relates to the preparation of necessary staring materials needed for a description of the present invention. It will be noted that this patent discloses the basic nucleus (II) (and derivatives thereof) upon which the present invention relies:

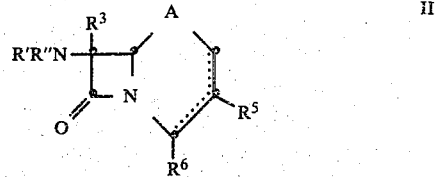

wherein all substituents are as previously defined and R' and R" are independently selected from the group consisting of hydrogen and acyl radicals known in the art. The incorporated by-reference application is: copending, commonly assigned U.S. Patent Application Ser. No. 587,526, filed June 16, 1975 now abandoned.

With reference to structure I, above-given, the preferred embodiments of the present invention are those wherein:

A is selected from the group consisting of S, O, $CH_2$, SO and $NR^7$; ($R^7$ is hydrogen, alkyl or acyl) X is selected from the group consisting of OH, SH, =O, =NH, $NH_2$ and $NH^7$;

$R^1$ and $R^2$ are independently selected from the group consisting of hydrogen, loweralkyl having from 1 to about 6 carbon atoms, aralkyl such as benzyl and phenethyl, heteroaralkyl such as 2-thienylmethyl, perfluoroalkyl, such as trifluoromethyl, and aryl such as phenyl and ring substituted aryl and ring and chain substituted aralkyl wherein the substituent is selected from the group consisting of lower alkyl, halogen such as Cl, Br, I or F, alkoxy, amino, carboxy, cyano, hydroxyl, and the like; $R^3$ is hydrogen, alkoxyl such as methoxyl, loweralkylthio such as methylthio and ethylthio and halogen such as fluoro and bromo;

$R^5$ is hydrogen, chloro, alkoxyl having 1 to 6 carbon atoms, formyl or $(CH_2)_nY$ wherein n is an integer 1 to 6 and Y is hydrogen, hydroxyl, halo, mercapto, acyloxy, acylthio, substituted hydroxy, substituted mercapto, a quaternary ammonium group, azido, amino or and N-substituted amino group. Thus, $(CH_2)_nY$ can be halomethyl such as chloromethyl, bromoethyl or fluoromethyl.

When Y is a substituted hydroxy or substituted mercapto group, $R^5$ can be shown by the formula

$(CH_2)_nZR'$ where Z is oxygen or sulfur, and R' is an acyl group; a straight chain or branched chain loweralkyl, alkenyl or alkynyl group; an aryl group; an aralkyl group; or a heterocyclic group such as heteroaryl or heteroalkyl. These groups can be unsubstituted or can be substituted by radicals such as alkyl, alkoxy, halo, cyano, carboxy, carbamoyl, azido, sulfo, amino, substituted amino, haloalkyl, carboxyalkyl, carbamoylalkyl, N-substituted carbamoylalkyl, quanidino, N-substituted guanidino, guanidoalkyl, sulfamyl, substituted sulfamyl, and the like. Representative of the groups thus represented that might be mentioned are methoxymethyl, n-propoxymethyl, methylthiomethyl, acetoxymethyl, propionyloxymethyl, benzoyloxymethyl, (p-chlorobenzoyl)oxymethyl, (p-methylbenzoyl)oxymethyl, pivaloyloxymethyl, (1-adamantyl)carboxymethyl, butanoyloxymethyl, carbamoyloxymethyl, (N-methylcarbamoyl)oxymethyl, (N-ethylcarbamoyl)oxymethyl, [N-(2-chlorethyl)carbamoyl]oxymethyl, (N-phenylcarbamoyl)oxymethyl, (N-p-sulfophenylcarbamoyl)oxymethyl, p-carboxyphenylphenylcarbamoyloxymethyl, methoxycarbonyloxymethyl, isobutanoyloxymethyl, cyclobutylcarbonyloxymethyl, carbamoylthiomethyl, (ethoxythiocarbonyl)thiomethyl, (n-propoxythiocarbonyl)thiomethyl, (cyclopentanoxythiocarbonyl)thiomethyl, methylthiomethyl, N,N-diethylthiocarbamoylthiomethyl, N-methylpiperazinium-1-thiocarbonylthiomethyl, N,N-dimethylpiperazinium-1-thiocarbonylthiomethyl, 2-furoylthiomethyl, isothiouroniummethyl, (5-methyl-1,3,4-thiadiazol-2-yl)thiomethyl, p-tolylsulfonylthiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl.

Alternatively, when $(CH_2)_nY$ is hydroxymethyl, (n=1), the cephalosporin can also exist as the lactone which is formed by internal esterification with the carboxy group.

The substituent $(CH_2)_nY$ can also be a group of the general formula:

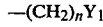

$-(CH_2)_nY_1$ wherein $Y_1$ represents amino or substituted amino including nitrogen heterocycles and substituted heterocyclic groups. Examples of such groups that might be mentioned are aminomethyl, acetamidomethyl, carbamoylaminomethyl, N,N-dimethylaminomethyl, N-(2-chloroethyl)aminomethyl, 5-cyanotriazol-1-ylmethyl, 4-methoxycarbonyltriazol-1-ylmethyl.

When Y is amino and n=1 the cephalosporin compound can also exist as the lactam formed by loss of water with the adjacent carboxy group.

Representative of the quaternary ammonium groups representing Y that might be mentioned are pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)pyridinium, 4-(trifluoromethyl)pyridinium, quinolinium, picolinium and lutidinium.

The preferred groups representing Y are hydrogen, halo, azido, cyano, hydroxy, alkoxy, aryloxy, aralkyloxy, heterocycloxy, mercapto, alkylthio, arylthio, aralkylthio, heterocyclicthio, amino, alkylamino, alkanoylamino, hydroxyphenyl, acylthio, acyloxy, isothiouronium, sulfamoyloxy, quaternary ammonium, a heterocyclic tertiary amine, alkylsulfonyloxy and (cis-1,2-epoxypropyl)phosphono. The heterocycles can be a 5 or 6 membered hetero ring containing one or more nitrogen, oxygen or sulfur atoms. The acyl group can be a loweralkanoyl group of 2-6 carbon atoms, carbamoyl, or thiocarbamoyl and N-alkyl or N,N-dialkyl derivatives thereof. The alkyl group of the foregoing substituents contains 1-6 carbon atoms and may be further substituted radicals such as alkoxy, halo, amino, cyano, carboxy, sulfo, and the like.

$R^6$ is $COXR^8$ wherein, X is oxygen or sulfur, and $R^8$ can be alkyl having 1-10 carbon atoms, straight or branched, such as methyl, ethyl, t-butyl, pentyl, decyl, etc.; substituted alkyl, wherein the alkyl portion has 1-10 carbon atoms but is preferably methyl or ethyl; and the substituent can be a heterocyclic structure having 1-3 hetero atoms of either O, N, or S; such as phthalimidomethyl, succinimidomethyl, phenacyl, p-bromophenacyl, (2-thienyl)methyl, (6-indenyl)methyl, acetoxyacetylmethyl, carboxymethyl, ethoxyethoxyethyl, (2-methylamino)ethyl, (2-diethylamino)ethyl, 2-(p-methylphenyl)sulfonylethyl, 2-(p-methylphenyl)ethyl, (2-acetamido)ethyl, etc. The substituent on the alkyl group can also be carboxyl, e.g., $R^8$ is $\alpha$-carboxy-$\beta,\beta$-dimethylpropyl; alkoxyalkyl wherein the alkoxy portion has 1-10 and preferably 1-6 carbon atoms, but can be branched, straight, or cyclic, and the alkyl portion has 1-6 carbon atoms, such as methoxymethyl, ethoxymethyl, isorpopoxymethyl, decyloxmethyl, ethoxypropyl, decyloxypentyl, cyclohexyloxymethyl, etc.; alkanoyloxyalkyl wherein the alkanoloxy portion is straight or branched and has 1-6 carbon atoms and the alkyl portion has 1-6 carbon atoms, such as acetoxymethyl, pivaloyloxymethyl, acetoxyethyl, propionyloxyethyl, acetoxypropyl, etc.; haloalkyl wherein halo is chloro, bromo, fluoro, or iodo, and the alkyl portion is straight or branched having 1-6 carbon atoms, e.g., 2,2,2-trichloroethyl, trifluoroethyl, 2-bromopropyl, diiodomethyl, 2-chloroethyl, 2-bromoethyl, etc.; alkenyl having 1-10 carbon atoms, either straight or branched, e.g., allyl, 2-propenyl, 3-butenyl, 4-pentenyl, 2-butenyl, 3-pentenyl, 2-methyl-2-propenyl, methallyl, etc.; alkynyl having 1-10 carbon atoms, either straight or branched, e.g., 3-pentynyl, propargyl, ethynyl, etc.; alkanoyl, either straight or branched, having 1-10 carbon atoms, such as pivaloyl, acetyl, propionyl, etc.; aralkyl wherein alkyl has 1-3 carbon atoms, such as benzyl, benzhydryl, and substituted benzyl or benzhydryl, e.g., o-nitrobenzyl, 3,4-dinitrobenzyl, p-methoxybenzyl, p-nitrobenzyl, 3,5-dichloro-4-hydroxybenzyl, p-methoxybenzhydryl, p-carboxybenzyl, the latter being either the free acid or the sodium salt, 2,4,6-trimethylbenzyl, p-(sodiumcarboxylate)benzyl, p-methylbenzyl, or phenylethyl, 2-(p-methylphenyl)ethyl, p-t-butylbenzyl, m-phenoxybenzyl, p-pivaloyloxybenzyl and the arylthioalkyl analogues; aryloxyalkyl wherein aryl is preferably a phenyl ring having 0–3 substituents, preferably 0 or 1 substituents in the ortho or para positions and alkyl is 1–6 carbon atoms, e.g., (4-methoxy)phenoxymethyl, phenoxymethyl, (4-chloro)phenoxymethyl, (4-nitro)phenoxymethyl, (4-benzyloxy)phenoxymethyl, (4-methyl)-phenoxymethyl, (2-methoxy)phenoxymethyl, (1-phenoxy)ethyl, (4-amino)phenoxymethyl, (4-methoxy)-phenylthiomethyl, (4-chloro)phenylthiomethyl, phenylthioethyl; aryl wherein aryl is phenyl or substituted phenyl having 0–3 substituents, preferably 0 or 1 substituent in the ortho or para position, e.g., (4-methyl)phenyl, (4-hydroxy)phenyl; aralkenyl wherein aryl is phenyl and alkenyl has 1–6 carbon atoms, such as 3-phenyl-2-propenyl; aralkoxyalkyl wherein aralkoxy is benzyloxy, and alkyl has 1–3 carbon atoms, such as benzyloxymethyl, (4-nitro)benzyloxymethyl, (4-chloro)-benzyloxymethyl; alkylthioalkyl wherein the alkylthio portion has 1–10 and preferably 1–6 carbon atoms, but can be branched, straight, or cyclic, and the alkyl portion has 1–6 carbon atoms, such as methylthioethyl, ethylthioethyl, cyclohexylthiomethyl, decylthiobutyl, methylthiopropyl, isopropylthioethyl, methylthiobutyl, etc.; or monocyclic aryl wherein aryl is phenyl, or substituted phenyl such as p-nitrophenyl, 3,5-dinitrophenyl, or p-carboxyphenyl, the latter having either the free acid or the sodium salt form.

In addition to the esters listed above, amides can also be employed, i.e., wherein X is the

groups, and $R^8$ is as defined.

Particularly preferred esters are those in formula I wherein X is oxygen and $R^8$ is aralkyl, aryloxyalkyl, aralkoxyalkyl, alkylthioalkyl, haloalkyl, or alkenyl.

It will be apparent from a further reading of this application that in many of the chemical reactions described, the cephalosporin is blocked at position 4 by a so-called "easily removable blocking group". Many of these groups are contained within the above definition of the chain —COXR$^8$. However, it has been found more convenient to use only relatively a few of these groups during such chemical reactions, then to remove the group to the free acid, and subsequently to react the latter with the desired alcohol to yield the suitable ester.

In this connection, it is noted that preferred "blocking groups" include the sub-generic groups defined above as aralkyl, haloalkyl, alkanoyloxyalkyl, alkoxyalkyl, alkenyl, substituted alkyl, or aralkoxyalkyl, and also include mono-, di-, and trialkylsilyl, wherein alkyl has 1–10 carbon atoms.

More specifically, preferred "blocking groups" include benzyl, phenacyl, methoxymethyl, trichloroethyl, trimethylsilyl, p-nitrobenzyl, p-bromophenyl, p-bromophenacyl, benzoylmethyl, p-methoxybenzyl, benzhydryl. These blocking groups are preferred since they are generally recognized easily-removable blocking groups in cephalosporin and penicillin art. Although we describe procedures for the removal of these blocking groups, such processes are considered within the skill of those in the art.

On the other hand, the novel cephalosporins of this invention are best utilized pharmacologically as either the free acid in the form of commonly used, non-toxic pharmaceutically acceptable salts, or certain of the above listed esters. For instance, esters belonging to the group defined as aralkyl, alkylthioalkyl, or alkenyl yield final products having outstanding oral activity. More specifically, high oral activity of the novel cephalosporins is obtained when $R^8$ is (2-methylthio)ethyl, 1-pivaloyloxymethyl, 3-phthalidyl, p-t-butylbenzyl, p-pivaloyloxybenzyl, m-phenoxybenzyl, benzyl, or 3-buten-yl.

By the term "non-toxic pharmaceutically acceptable salts" is meant salts that are suitable for isolating, purifying and/or marking purposes, for example salts with bases or with acids, as well as inner salts. Salts with bases are in the first place metal salts, especially alkali metal salts, for example sodium or potassium salts, or alkaline earth metal salts, for example magnesium or calcium salts, or ammonium salts, including ammonium salts with organic bases such as tri-lower alkylamines, for example trimethylamine or triethylamine, or N-lower alkylazacycloalkanes, for example 1-methyl-pyrrolidine or 1-ethyl-piperidine, also dibenzylethylenediamine or procaine. They are obtained, for example, by treating the free compounds or inner salts with the basic compounds, as desired with the aid of an ion exchange resin.

Acid addition salts are in the first place those with strong inorganic acids, such as hydrochloric hydrobromic or sulphuric acid, or with strong organic acids such as strong organic sulphonic acids, for example, methanesulphonic, 2-hydroxyethanesulphonic or p-toluenesulphonic acid, or with a strong organic carboxylic acid, for example trifluoroacetic acid. They can be obtained, for example, by treating the free compounds with the appropriate strong acids if desired with the aid of an ion exchange resin.

Inner salts, which appear as hybrid ions, are obtained by treating an acid additon salt with an appropriate, weakly basic ion exchange resin, or by titrating with a base up to the isoelectric point, or from a salt with a base by treatment with acid.

The most preferred embodiments of the present invention are those wherein:

A is S, O, CH$_2$ and SO;

X is OH;

$R^1$ and $R^2$ are independently selected from the group consisting of hydrogen, substituted and unsubstituted lower alkyl having from 1–6 carbon atoms, aryl such as phenyl, and substituted phenyl and aralkyl such as β-phenethyl, 1-hydroxy, 1-amino-, 1-carboxyethyl benzene, and benzyl and heteroalkyl such as 2-thienylmethyl, wherein the above ring and chain substituents are selected from the group consisting of COOH, NH$_2$, OH and the like;

$R^3$ is hydrogen or methoxyl;

and $R^5$ and $R^6$ are as defined above.

In general the compounds of the present invention are prepared according to the following reaction scheme:

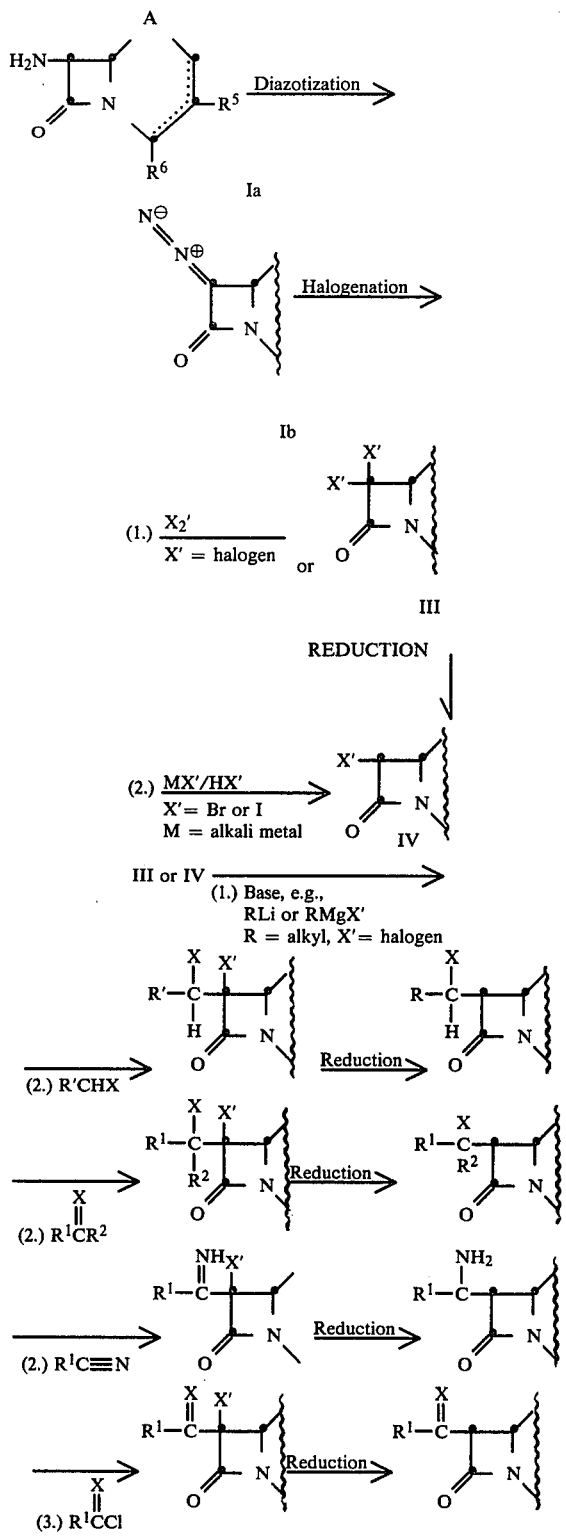

In words relative to the above reaction diagram, the free 7-amino species, Ia, is diazotized by conventional procedures such as by reaction with NaNO₂ in the presence of acid such as 2 N sulfuric acid in a solvent such as methylene chloride or the like at a temperature of from 0° C. to about 25° C. for from a few minutes to 4 hours. The resulting diazo derivative, Ib, isolated by conventional procedures such as extraction followed by organic solvent removal, is then halogenated by either of two procedures. Both are well-known. The first procedure provides the 7,7-dihalo species, III, and involves direct halogenation, such as bromination, in a solvent such as methylene chloride or the like at a temperature of from −78° to about 0° C. for from a few minutes to about 4 hours. The second procedure provides the mono halo species, IV, preferably the 7-iodo or 7-bromo species and is conducted in a polar solvent such as water, acetone, alcohol or aqueous mixtures thereof in the presence of the halide salt and its corresponding acid. The reaction is conducted at from 0° to about 25° C. for from a few minutes to 4 hours. Products, III and IV, if desired are separated by conventional procedures involving solvent extraction, concentration, and chromatography. It should be noted that III is convertible to IV by reduction. A particularly suitable reduction is effected by a Zn and Ag couple in methanol according to reported procedures, such as R. D. Clark and C. H. Heatcock, J. Org. Chem., 38, 3658 (1973); alternatively catalytic hydrogenation employing Pd/C, Pd/CaCO₃ or PtO₂ in solvents such as alcohols, ethylacetate or dioxane at about 0° to 25° C. under 1 to 50 atmospheres hydrogen.

Intermediate products, III and IV, are converted to the final products of the present invention by contacting either with a base such as an organo metallic base such as a lithium alkyl or a Grignard reagent RMgX' wherein R is alkyl or aryl, or the like, and X' is halogen such as bromo and thereafter adding to the reaction mixture the reagent of choice to give the desired final product. The reagents, as shown in the diagram are: H₂CO, R¹CHX,

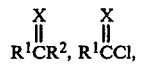

and R¹C≡N; wherein R¹ and R² are as defined above, and X is oxygen or sulphur. Typically the reaction is conducted in a solvent such as tetrahydrofuran, ether, dimethoxyethane, or mixtures thereof or the like at a temperature of from −100° to about 0° C. for from a few minutes to about 4 hours. Typically, the organo metallic base is added first. Products derived from the 7,7-dihalo species, III, yield the illustrated halohydrins which are reduced to the final products, I, by conventional techniques such as catalytic reduction or zinc-silver couple in methanol.

It is to be noted that the above reaction scheme is regio-specific for the 7-position and that there are no criticalities of reaction parameters other than those set forth above and elaborated upon in the following specific examples. It should be further noted that the above-described procedure provides all embodiments of the present invention except those wherein R³ is other than hydrogen. When R³ is alkoxy or alkylthio such as methoxyl or methylthio, for example, the above procedure is modified by a subsequent procedure which involves derivatization of the 7-substituted methyl species (R³=H) to form those species of the present invention wherein R³ is, for example, methoxyl. The following diagram illustrates such schemes:

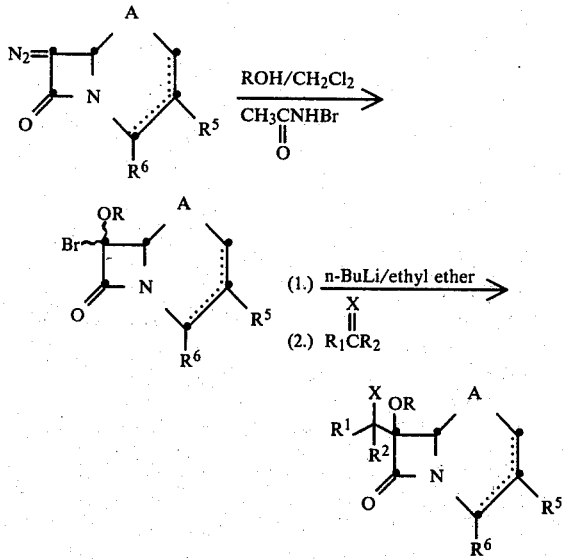

SCHEME I

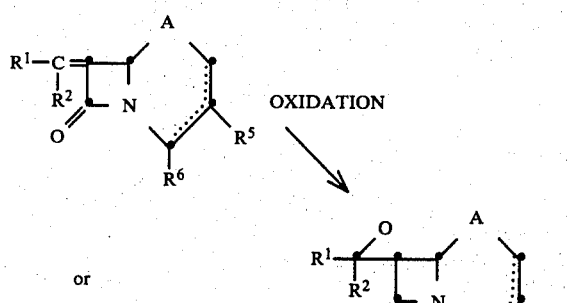

SCHEME II

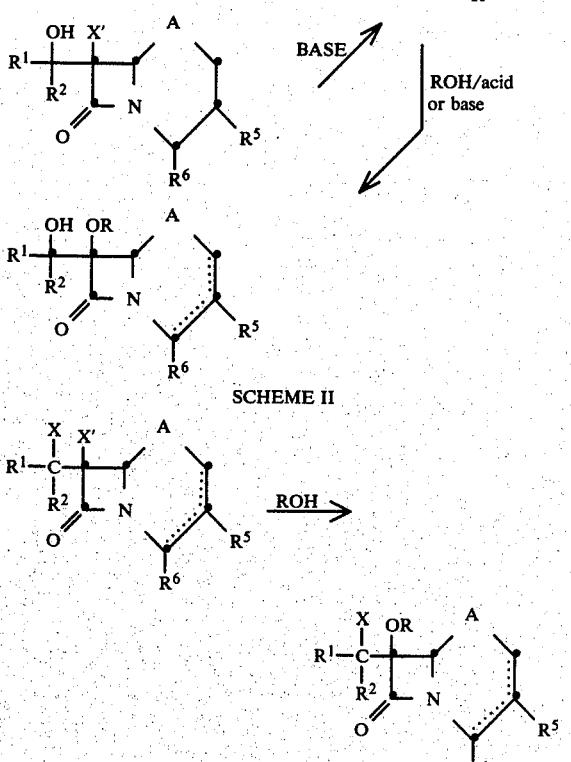

-continued
SCHEME III

With respect to the above Schemes I–III, all symbolism is as previously defined and ROH (which may also be RSH) designates a lower alkanol (or lower alkyl thio); thus in the final products —OR designates the substituent $R^3$.

In Scheme I, the diazo starting material is available to the art. Typically the first step of the reaction is conducted in a solvent medium such as ROH or a mixture (ROH/$CH_2Cl_2$, 1:1) of ROH and a solvent such as $CH_2Cl_2$, acetonitrile, benzene or the like containing 1 to about 3 equivalents of a brominating agent such as N-bromoacetamide, N-bromosuccinimide or the like; typically the reaction is conducted at from about 0° to about 50° C. for from a few minutes to several hours. The resulting 7-bromo-7-$R^3$ species are known as is the above described process. The 7-bromo-7-$R^3$ species is then treated with a base 1.0 to 1.5 equivalents) such as an organo-metallic base, for example, n-butyl lithium, methylmagnesium bromide or the like in a solvent such as diethyl ether, tetrahydrofuran, dimethoxyethane or the like at a temperature of from $-80°$ C. to about 0° C.; and thereafter adding, as above-described, the reagent of choice ($R^1CHX$,

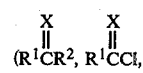

$R^1C\equiv N$ or

to give the desired final product.

The epoxide of Scheme II may be prepared by treatment of the olefin with an oxidizing agent such as a per acid or an alkaline peroxide solution or directly from the 6-halo species by treatment with base. The resulting epoxide is then converted to the desired product by treatment with an alcohol in the presence of acid or base. Suitable oxidizing agents are alkaline hydrogen peroxide or m-chloropenbenzoic acid and the like. Typically the oxidation is conducted with m-chloroperbenzoic acid in a solvent such as methylene chloride, benzene, dioxane or tetrahydrofuran at a temperature of from $-20°$ to 50° C., for from a few minutes to several hours. Direct conversion of the 7-halo species to the oxide is effected in solvents such as methanol, methylene chloride, acetonitrile and tetrahydrofuran in the presence of 1.0 to 2.0 equivalents of a base such as sodium methoxide, triethylamine, lithium diiopropylamide and sodium hydride at $-20°$ to 50° C., for from a few minutes to several hours. Conversion of the oxide to the desired product is typically conducted in the alcohol of choice or in a mixture of ($CH_2Cl_2$/ROH,1:1) of the alcohol with a solvent such as methylene chloride, acetonitrile, benzene and tetrahydrofuran in the presence of a base (1 to 2 equivalents) such as sodium methoxide, or triethylamine, and the like, at $-78°$ to 22° C. for from a few minutes to several hours. The oxide may be converted to the desired product by treatment in acidic solution. It is to be noted that the olefin starting material is known.

Scheme III is conducted by treating the 7-halo species in the alcohol of choice, for example methanol, ethanol or a mixture of alcohol with some other solvent such as methylene chloride, acetonitrile or tetrahydrofuran with a reagent such as silver tetrafluoroborate at a temperature of from 0° to 50° C. for a few minutes to overnight.

The present invention embraces all stereoisomers of the compounds prepared by the above processes. However, it is well-known in the bicyclic β-lactam antibiotic art that certain isomers of a given species are more active than their corresponding enantiomorph. This appears to be true for the instant invention; although the extent of this relationship of antibiotic activity to configuration cannot be stated for all species embraced by the present invention. However, by way of illustration, the following relationship has been established for the species 7-(1-hydroxyethyl) cephalosporanic acid (I):

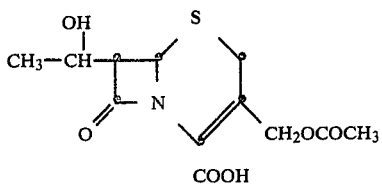

Because of the regio-specific synthesis, detailed above there are only 4 steroisomers of interest:

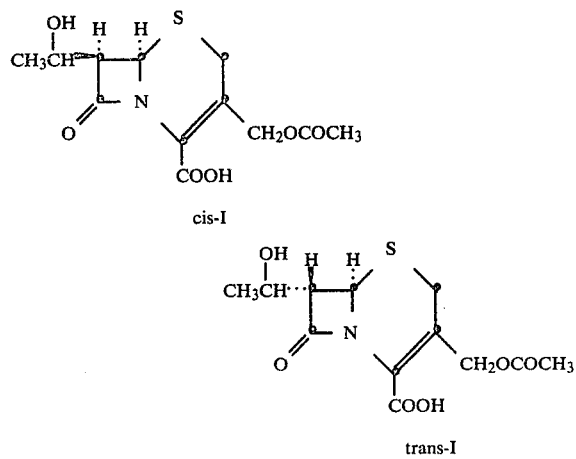

For each configuration, cis or trans, there are two stereoisomers. For example, relative to the cis configuration there are the following diastereomers:

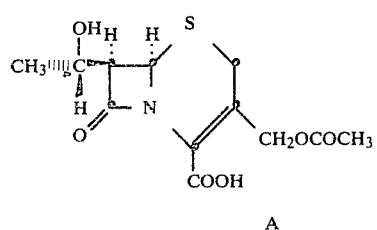

A

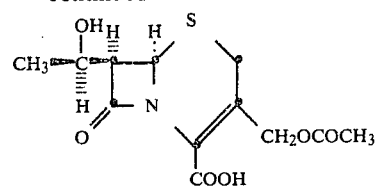

B

Correspondingly, there are two trans isomers. The absolute configuration of the isomers at the side chain carbon is not known, however, any given isomer may unambiguously be identified by physical parameters. In the specific case of the above-illustrated species all isomers appear active, however, the cis isomers, designated A and B (above), are preferred as having higher activity.

Pharmaceutically acceptable salts which may be formed using procedures well known to the art from the compounds of the invention include (a) inorganic base salts such as alkali metal, e.g. sodium and potassium, alkaline earth, e.g. calcium, and organic base salts, e.g. procaine and dibenzylethylene diamine salts and (b) acid addition salts, e.g. with hydrochloric, hydrobromic, sulphuric, nitric, phosphoric, toluene-p-sulphonic and methanesulphonic acids. In addition to salts, the novel compounds of the present invention may be administered in the form of esters, including those discussed above. Examples of esters that might be mentioned are esters of alcohols, phenols, mercaptans, and thiophenols of the general formula —COOR$^8$ wherein R$^8$ represents the radical of an alcohol or a thiol such as methyl, ethyl, tertiary butyl, a substituted alkyl such as phthalimidomethyl, succinimidomethyl, phenacyl, a substituted phenacyl for example p-bromophenacyl, a β-substituted ethyl group such as 2,2,2-trichloroethyl, 2-(p-methylphenyl)ethyl, 2-(p-methylphenyl)sulfonylethyl, 2-methylaminoethyl, methylthioethyl, 2-chloro(or bromo)ethyl, benzyl, a substituted benzyl group such as p-nitrobenzyl, m-phenoxybenzyl, p-pivaloyloxybenzyl, benzyloxybenzyl, p-t-butylbenzyl, p-methoxybenzyl, 3,5-dinitrobenzyl, 2,4,6-trimethylbenzyl, 3,5-dichloro-4-hydroxybenzyl, and the like, a benzhydryl or substituted benzhydryl group such as p-methoxybenzhydryl, an acyloxy alkyl group such as acetoxymethyl, pivaloyloxymethyl, or ethyl, an alkoxy group such as methoxymethyl, aryloxymethyl such as phenoxymethyl, or a monocyclic aryl group for example phenyl or substituted phenyl such as p-nitrophenyl or 3,5-dinitrophenyl or unsaturated alkyl such as 3-methylbutenyl, methallyl, 3-butenyl, and the like. These esters are readily prepared in accordance with processes well known in the art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus* (penicillin resistant), *Escherichia coli, Klebsiella pneumoniae, Salmonella typhosa,* Pseudomonas and *Bacterium proteus*. The compounds of the present invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose aluminum stearate gel or hydrogenated edible fats, emulsifying agents, for example lecithin, sorbitan monooleate or acacia; non-aqueous vehicles, which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being teated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. by weight of active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution. Typical formulations of specific products are described below.

The following examples representatively illustrate; but do not limit the product, process, compositional or method of treatment aspects of the present invention.

EXAMPLE I

Preparation of 7-[1'-hydroxyethyl]cephalosporanic Acid

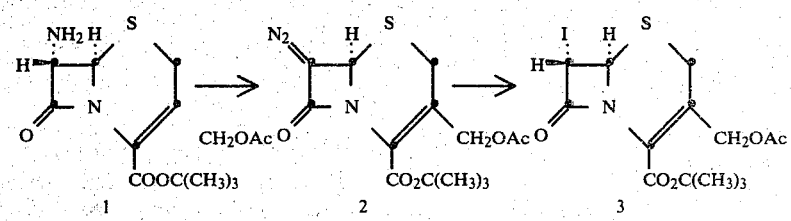

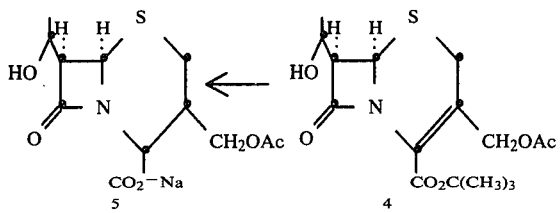

Step A

Preparation of t-butyl-7-diazocephalosporanate (2)

A mixture of 2.7 g. (8.36 mmoles) of t-butyl 7-aminocephalosporanate (1) prepared according to the literature procedure [R. J. Stedman, *J.Med.Chem.*, 9, 444 (1966)] and 1.15 g. (16.7 mmoles) of sodium nitrile in 120 ml. of methylene chloride and 120 ml. water is cooled to 0° C.-3° C. in an ice/H$_2$O bath and is treated with 6.24 ml. of 2 N sulfuric acid for 50 minutes. The organic phase is separated, dried with anhydrous sodium sulfate, filtered, and concentrated. The concentrate is used immediately for subsequent transformation.

Step B

Preparation of t-butyl 7-α-iodocephalosporanate (3)

The concentrate of t-butyl 7-diazocephalosporanate (2) obtained from process I is diluted with 180 ml. of acetone, cooled to 0° C.-3° C. in an ice/H$_2$O bath, and treated with a cold solution of 3.7 ml. of 57% hydroiodic acid and 4.76 g. of sodium iodide in 15 ml. of water for 25 minutes. After this time, the mixture is treated with solid sodium bicarbonate, filtered, and evaporated. The residue obtained is partitioned between 150 ml. of ethyl acetate and 125 ml. of 5% aqueous sodium thiosulfate and shaken vigorously. The organic phase is separated, dried with anhydrous magnesium sulfate, and evaporated. Purification by column chromatography on 150 g. of Florosil using benzene-ethyl acetate ((10:1) as the eluant gives 1.0 g. (27%) of product 3, which is identified by NMR spectral analysis.

Step C

Preparation of t-butyl 7-α and 7-β-[1'-hydroxyethyl]cephalosporanates (4) as Diastereomeric Mixtures A stirred solution of t-butyl 7-α-iodocephalosporanate (3) 137.5 mg. (0.3 mmoles) in 10 ml. of anhydrous diethyl ether at −70° C. under nitrogen atmosphere is treated with one molar equivalent of a solution of 2.9 M methylmagnesium bromide in diethyl ether for 10 minutes. The resulting suspension is then exposed to excess anhydrous acetaldehyde at −70° C. for 15 minutes followed by stirring for an additional 45 minutes. The reaction mixture is quenched at −70° C. with 1.0 ml. of saturated aqueous ammonium chloride and partitioned between diethyl ether and water. The organic phase is separated, dried with anhydrous magnesium sulfate, filtered, and evaporated. Purification of the residue obtained by preparative thin layer chromatography [2 developments benzene-EtOAc (4:1)] gives 19.0 mg. of t-butyl 7-β-[1'-hydroxyethyl]cephalosporanate as a single, crystalline diastereomer; m.p. 154.5° C.-155.5° C. (isopropanol); identified by NMR; and 27.5 mg. of t-butyl 7-α-[1'-hydroxyethyl]cephalosporanate as a mixture of both diastereomers which are separated by high pressure liquid chromatography and characterized by NMR spectroscopy.

Step D

Preparation of Sodium 7-β-[1'-hydroxyethyl]cephalosporanate (5)

t-Butyl 7-β-[1'-hydroxyethyl]cephalosporanate (4) 33.0 mg. (0.09 mmoles) is dissolved in 1.0 ml. of cold trifluoroacetic acid and the mixture is stirred at 0° C. for 30 minutes. The trifluoroacetic acid is removed under reduced pressure and the residue obtained is partitioned between chloroform and dilute aqueous sodium bicarbonate. The aqueous phase is separated and acidified to pH 1.5 with 2.5 N hydrochloric acid and is extracted with ethyl acetate. The ethyl acetate extract is dried with anhydrous magnesium sulfate, filtered, and evaporated to give 27.0 mg. (97%) of 7-β-[1'-hydroxyethyl]-cephalosporanic acid which is characterized by IR, NMR, and mass spectrum (as ditrimethylsilyl derivative).

The cephalospranic acid is converted to its corresponding sodium salt by treating an aqueous acetone solution of the acid with a solution of one molar equivalent of sodium bicarbonate in water, removing the acetone under reduced pressure, and lyophilizing the aqueous solution.

In similar fashion each of the other three t-butyl-7-[1-hydroxyethyl]cephalosporanate isomers are converted to the corresponding sodium 7-(1-hydroxyethyl)cephalosporanate.

EXAMPLE 3

Preparation of Benzhydryl (and t-Butyl) 7-methoxy-7-(1-hydroxyethyl)-Cephalosporanate

Step A

Preparation of benzhydryl 7,7-dibromocephalospornate

To a stirred solution of freshly prepared benzhydryl 7-diazocephalosporanate (1.03 g., 2.3 mmoles) in 75 ml. methylene chloride at −70° under nitrogen atmosphere is added dropwise a solution of bromine (368 mg., 2.3 mmole) in 20 ml. methylene chloride during 15 minutes. The mixture is warmed to 0° during 20 mins. and evaporated under reduced pressure. The residue is purified by column chromatography on silica gel to give 280 mg. (21%) benzhydryl 7,7-dibromocephalosporante. Recrystallization from CH$_2$Cl$_2$—Et$_2$O gives m.p. 127° (dec.).

Analysis Calc. for C$_{23}$H$_{19}$NO$_5$SBr$_2$: Calc.: C, 47.52; H, 3.29; N, 2.41; Br, 27.49. Found: C, 47.62; H, 3.22; N, 2.38; Br, 27.46.

In similar fashion t-butyl-7-diazocephalosporanate is converted to t-butyl 7,7-dibromocephalosporanate.

Step B

Preparation of t-butyl 7-bromo-7-(1-hydroxyethyl)cephalosporanate

By substitution of t-butyl 7,7-dibromocephalosporanate for t-butyl 7-α-iodocephalosporanate in the procedure described in Step C of Example 1 the product obtained is t-butyl 7-bromo-7-(1-hydroxyethyl)cephalosporanate. The corresponding benzhydryl ester is similarly converted to benzhydryl 7-bromo-7-(1-hydroxyethyl)cephalosporanate.

Step C

Preparation of t-butyl 7-methoxy-7-(1-hydroxyethyl)cephalosporate

To a stirred solution of 1 g. (0.229 mmole) of t-butyl 7-bromo-7-(1-hydroxyethyl)cephalosporanate in 20 ml. of methanol under nitrogen at 22° C. is added 0.45 g. (0.229 mmole) of silver tetrafluoroborate. Progress of the reaction is followed by thin layer chromatography. When the reaction is complete the solution is evaporated under reduced pressure and the residue is purified by column chromatography on silica gel using mixtures of benzene and ethyl acetate.

The benzhydryl ester is similarly converted.

Step D

Preparation of benzhydryl 7-bromo-7-methoxycephalosporanate

A solution of benzhydryl 7-diazocephalosporanate (0.45 g., 1.0 mmole) in 10 ml. of methanol and 10 ml. methylene chloride containing 0.138 g. (1.0 mmole) of N-bromoacetamide is stirred at 22° C. until reaction is complete. The solvents are removed under reduced pressure and the residue is chromatographed using ethyl acetate-benzene mixtures to afford the desired benzhydryl 7-bromo-7-methoxycephalosporanate.

Step E

Preparation of benzhydryl 7-(1-hydroxyethyl)-7-methoxycephalosporanate

Benzhydryl 7-bromo-7-methoxycephalosporanate is treated with n-butyllithium followed by acetaldehyde according to the procedure of Example 1, Step C to afford the desired benzhydryl 7-(1-hydroxyethyl)-7-methoxycephalosporante.

EXAMPLE 4

The following chart illustrates the preparation of representative species of the present invention by way of analogy to relevant foregoing examples by substituting, in equivalent amounts, for the reagents of the analogous example.

| Compound | $R^1$ | $R^2$ | $R^3$ | A | $R^5$ | $R^6$ | X |
|---|---|---|---|---|---|---|---|
| 1 | $CH_3$ | H | H | S | $CH_2OAc$ $Ac = -\overset{O}{\underset{\|}{C}}CH_3$ | $COOCHPh_2$ Ph = phenyl | OH |
| 2 | H | H | H | S | $CH_2OAc$ | COOtBu | OH |
| 3 | $CH_3$ | H | OMe | S | $CH_2OCNH_2$ (O) | COO-t-butyl | OH |
| 4 | Ph–CH$_2$–CH$_2$– | H | H | S | $CH_2OAc$ | $COOCHPh_2$ | OH |
| 5 | Ph–CH(NH$_2$)–CH$_2$– | $CH_3$ | H | O | $CH_2S$–(triazole with N–Me) | COOTMS TMS = trimethylsilyl | OH |
| 6 | (thiophene)–CH$_2$CH$_2$– | H | SMe | N | H | $COOCH_2CCl_3$ | OH |
| 7 | Ph–CH(COOH)–CH$_2$– | — | H | $CH_2$ | $CH_3$ | COOTMS | =O |
| 8 | Ph–CH(OH)–CH$_2$– | H | Br | SO | H | COOTMS | $-NH_2$ |

EXAMPLE 5

Preparation of Pharmaceutical Compositions

One such unit dosage form consists in mixing 120 mg. of 7β-(1'-hydroxyethyl)cephalosporanic acid with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 7β-(1'-hydroxyethyl)cephalosporanic acid | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 7β-(1'-hydroxyethyl)cephalosporanic acid | 500 mg. |
| Diluent: Sterile Water for Injection | 2 cc. |
| OPTHALMIC SOLUTION | |
| 7β-(1'-hydroxyethyl)cephalosporanic acid | 100 mg. |
| Hydroxypropylmethyl Cellulose | 5 mg. |
| Sterile Water to | 1 ml. |
| OTIC SOLUTION | |
| 7β-(1'-hydroxyethyl)cephalosporanic acid | 100 mg. |
| Benzalkonium Chloride | 0.1 mg. |
| Sterile Water to | 1 ml. |
| TOPICAL OINTMENT | |
| 7β-(1'-hydroxyethyl)cephalosporanic acid | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

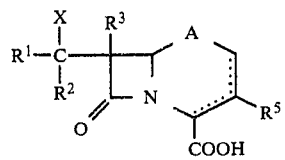

and the non-toxic, pharmaceutically acceptable salts thereof; wherein:
the dotted line indicates provision for both $\Delta^2$ and $\Delta^3$ embodiments:
A is S and SO;
$R^3$ is hydrogen, methoxyl, and lower alkylthio;
X is OH, SH, $NH_2$, $=O$ and $=NH$;
$R^1$ and $R^2$ are independently selected from the group consisting of hydrogen, lower alkyl, benzyl, phenethyl, 2-thienylmethyl, and phenyl;
$R^5$ is hydrogen, chloro, lower alkoxy, formyl and $-(CH_2)_nY$ wherein n is an integer from 1–6 and Y is hydrogen, hydroxy, halogen, lower alkanoyloxy, lower alkanoylthio, lower alkoxy, phenoxy, benzyloxy, azido, amino, N-lower alkylamino, N,N-dilower alkylamino, N-lower alkanoylamino, N,N-dilower alkanoylamino, carbamoyl or thiocarbamoyl and the N-lower alkyl or N,N-dilower alkyl derivatives thereof, pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)pyridinium, 4-(trifluoromethyl)-pyridinium, quinolinium, and luthidinium; with the proviso that, when X is $=O$ or $=NH$, one of $R^1$ and $R^2$ is absent, and that not all of $R^1$, $R^2$, $R^3$ and $R^5$ are hydrogen at the same time.

2. The $\Delta^3$ compound of claim 1 wherein A is S and X is OH.

3. A pharmaceutical composition comprising a therapeutically effective amount, in unitary dosage form, of a compound according to claim 1 and a pharmaceutical carrier therefor.

* * * * *